United States Patent [19]

Rosen et al.

[11] Patent Number: 5,580,862
[45] Date of Patent: Dec. 3, 1996

[54] SULFATE LIGANDS FOR L-SELECTINS AND METHODS OF PREVENTING SULFATE ADDITION

[75] Inventors: Steven D. Rosen, San Francisco, Calif.; Yasuyuki Imai, Tokyo, Japan

[73] Assignee: The Regents of the University of California, Oakland, Calif.

[21] Appl. No.: 422,639

[22] Filed: Apr. 14, 1995

Related U.S. Application Data

[63] Continuation of Ser. No. 943,817, Sep. 11, 1992, abandoned.

[51] Int. Cl.$^6$ .................... A61K 31/715; A61K 31/73; A61K 31/735; C07H 3/06
[52] U.S. Cl. .................... 514/61; 514/25; 514/54; 536/17.5; 536/54; 536/55.1; 536/55.2; 536/123.1
[58] Field of Search .................. 424/1.11, 9.35, 424/234.1; 514/25, 54, 61; 536/17.5, 54, 55.1, 55.2, 123.1

[56] References Cited

U.S. PATENT DOCUMENTS

| | | | |
|---|---|---|---|
| 4,163,783 | 9/1979 | Klein et al. | 424/245 |
| 4,370,325 | 1/1983 | Packman | 424/245 |
| 5,013,724 | 5/1991 | Petitou et al. | 514/54 |
| 5,143,712 | 9/1992 | Brandley et al. | 424/1.1 |

FOREIGN PATENT DOCUMENTS

WO92/02527 2/1992 WIPO.

OTHER PUBLICATIONS

Imai, Y. et al., "Sulphation Requirement for GlyCAM–1, an Endothelial Ligand for L–Selectin," *Nature* (1993) 361:555–557.
"Potassium Chlorate," *Martindale, The Extra Pharmacopoeia* Micromedex, Inc., vol. 78.
"Sodium Chlorate," *Martindale, The Extra Pharmacopoeia* Micromedex, Inc., vol. 78.
"Pastilles M.B.C.," *CD–ROM Vidal*, O.V.P.—editions du Vidal, Paris, 1992.
"Gargarisma" *Rote Liste*, Budesverband der Pharmazeutschen Industrie E.V., Edition Cantor, Aulendorf, 1992.
Lasky, L. A., "Lectin Cell Adhesion Molecules (LEC–CAMs): A New Family of Cell Adhesion Proteins Involved with Inflammation" *J. Cell. Biochem.* (1991) 45(2):139–146.
Brandley, et al., "Cell–Surface Carbohydrates in Cell Recognition and Response," *J. Leuk. Biol.*, (1986) 40:97–111.
Sharon, et al., "Lectins as Cell Recognition Molecules," *Science*, (1989) 246:227–234.
Dodd, et al., "Lactoseries Carbohydrates Specify Subsets of Dorsal Root Ganglion Neurons Projecting to the Superficial Dorsal Horn of Rat Spinal Cord," *J. Neurosci.*, (1985) 5(12):3278–3294.
Regan, et al., "Selective Expression of Endogenous Lactose–binding Lectins and Lactoseries Glycoconjugates in Subsets of Rat Sensory Neurons," *Proc. Natl. Acad. Sci. USA* (1986) 83:2248–2252.
Constantine–Paton, et al., "A Cell Surface Molecule Distributed in a Dorsoventral Gradient in the Perinatal Rat Retina," *Nature*, (1986) 324:459–462.
Tiemeyer, et al., "Ganglioside-specific Binding Protein on Rat Brain Membranes," *J. Bio. Chem.*, (1989) 264(3):1671–1681.
Bevilacqua, et al., "Identification of an inducible Endothelial–Leukocyte Adhesion Molecule," *Proc. Natl. Acad. Sci. USA*, (1987) 84:9238–9242.
Fukuda, et al., "Structure of a Novel Sialylated Fucosyl Lacto-N-nor-hexaosylceramide isolated from Chronic Myelogenous Leukemia Cells," *J. Biol. Chem.*, (1986) 261(5):2376–2383.
Magnani, et al., "A Monoclonal Antibody–defined Antigen Associated with Gastrointestinal Cancer is a Ganglioside Containing Sialylated Lacto–N–fucopentaose II," *J. Biol. Chem.*, (1982) 257(23):14365–14369.
Hakomori, et al., "Human Cancer–Associated Gangliosides Defined by a Monoclonal Antibody (IB9) Directed to Sialosylα2→6 Galactosyl Residue: A Preliminary Note," *Biochem. and Biophys. Res. Comm.*, (1983) 113(3):791–798.
Fukushi, et al., "Localization and Alteration of Mono–, Di–, and Trifucosylα1→3 Type 2 Chain Structures During Human Embyrogenesis and in Human Cancer," *J. Exp. Med.*, (1984) 159:506–520.
Geng, et al., "Rapid Neutrophil Adhesion to Activated Endothelium Mediated by GMP–140," *Nature*, (1990) 343:757–760.
Johnston, et al., "Cloning of GMP–140, a Granule Membrane Protein of Platelets and Endothelium: Sequence Similarity to Proteins Involved in Cell Adhesion and Inflammation," *Cell*, (1989) 56:1033–1044.
Geoffroy, et al., "Demonstration that a Lectin–like Receptor ($gp90^{MEL}$) Directly Mediates Adhesion of Lymphocytes to High Endothelial Venules of Lymph Nodes," *J. Cell. Biol.*, (1989) 109:2463–2469.
Lasky, et al., "Cloning of a Lymphocyte Homing Receptor Reveals a Lectin Domain," *Cell*, (1989) 56:1045–1055.

(List continued on next page.)

*Primary Examiner*—John W. Rollins
*Assistant Examiner*—Francisco C. Prats
*Attorney, Agent, or Firm*—Karl Bozicevic; Fish & Richardson P.C.

[57] ABSTRACT

Sulfated oligosaccharides which bind to selectin receptors and act as agonists are formulated into pharmaceutical formulations and administered by injection to treat inflammation. Compounds such as chlorates which act as metabolic inhibitors of carbohydrate sulfation and inhibit the sulfation of naturally occurring ligands for selectin receptors are administered locally by injection to alleviate and/or prevent inflammation. Sulfatase is administered which removes a sulfate moiety from a natural sulfated ligand. The sulfated oligosaccharides can be administered in combination with the chlorates and sulfatases in order to obtain a combined effect which is useful in preventing and/or alleviating inflammation.

2 Claims, 2 Drawing Sheets

OTHER PUBLICATIONS

Bevilacqua, et al., "Endothelial Leukocyte Adhesion Molecule 1: An Inducible Receptor for Neutrophils Related to Complement Regulatory Proteins and Lectins," *Science*, (1989) 243:1160–1165.

Watson, et al., "Neutrophil Influx into an Inflammatory Site Inhibited by a Soluble Homing Receptor–IgG Chimaera," *Nature*, (1991) 349:164–167.

Spertini, et al., "Regulation of Leukocyte Migration by Activation of the Leukocyte Adhesion Molecule–1 (LAM–1) Selectin," *Nature*, (1991) 349:691–694.

Imai, et al., "Direct Demonstration of the Lectin Activity of gp90$^{MEL}$, a Lymphocyte Homing Receptor," *J. Cell. Biol.*, (1990) 111:1225–1232.

Imai, et al., "Identification of a Carbohydrate–based Endothelial Ligand for a Lymphocyte Homing Receptor," *J. Cell. Biol.*, (1991) 113(5):1213–1221.

Lerouge, et al., "Symbiotic Host–specificity of *Rhizobium meliloti* is Determined by a Sulphated and Acylated Glucosamine Oligosaccharide Signal," *Nature*, (1990) 344:781–784.

Fiete, et al., "A Hepatic Reticuloendothelial Cell Recepetor Specific for $SO_4$–4GalnAcβ1, 4GlcNAcβ1, 2Manα That Mediates Rapid Clearance of Lutropin," *Cell*, (1991) 67:1103–1110.

Baeuerle, et al., "Chlorate–A Potent Inhibitor of Protein Sulfation in Intact Cells," *Biochem. and Biophys. Res. Comm.*, (1986) 141(2):870–877.

Gallatin, et al., "A Cell–Surface Molecule Involved in Organ–Specific Homing of Lymphocytes," *Nature*, (1983) 304:30–34.

Stoolman, "Adhesion Molecules Controlling Lymphocyte Migration," *Cell*, (1989) 56:907–910.

Yednock, et al., "Phosphomannosyl–derivatized Beads Detect a Receptor Involved in Lymphocyte Homing," *J. Cell. Biol.*, (1987) 104:713–723.

Yednock, et al., "Receptors Involved in Lymphocyte Homing: Relationship Between a Carbohydrate–binding receptor and the MEL–14 Antigen," *J. Cell. Biol.*, (1987) 104:725–731.

Bevilacqua, et al., "Selectins: A Family of Adhesion Receptors," *Cell*, (1991) 67:233.

Lasky, et al., "An Endothelial Ligand for L–Selectin is A Novel Mucin–like Molecule," *Cell*, (1992) 69:927–938.

Rosen, et al., "Involvement of Sialic Acid on Endothelial Cells in Organ–Specific Lymphocyte Recirculation," *Science*, (1985) 228:1005–1007.

Imai, et al., "Further Characterization of the Interaction Between L–selectin and its Endothelial Ligands," *Glycobiology*, (1992) 2(4):373–381.

Siegelman, et al., "Mouse Lymph Node Homing Receptor cDNA Clone Encodes a Glycoprotein Revealing Tandem Interaction Domains," *Science*, (1989) 243;1165–1172.

Tedder, et al., "Isolation and Chromosomal Localization of cDNAs Encoding a Noval Human Lymphocyte Cell Surface Molecule LAM–1," *J. Exp. Med.*, (1989) 170:123–133.

Camerini, et al., "Leu–8/TQ1 is the human equivalent of the Mel–14 lymph node homing receptor," *Nature*, (1989) 342:78–82.

Stoolman, et al., "Possible Role for Cell–surface Carbohydrate–binding Molecules in Lymphocyte Recirculation," *J. Cell. Biol.*, (1983) 96:722–729.

Berg, et al., "The Human Peripheral Lymph Node Vascular Addressin is a Ligand for LECAM–1, the Peripheral Lymph Node Homing Receptor," *J. Cell. Biol.*, (1991) 114(2):343–349.

Streeter et al., "Immunohistologic and Functional Characterization of a Vascular Addressin Involved in Lymphocyte Homing into Peripheral Lymph Nodes," *J. Cell Biol.*, (1988) 107:1853–1862.

Rapraeger, et al., "Requirement of Heparan Sulfate for bFGF–Mediated Fibroblast Growth and Myoblast Differentiation," *Science*, (1991) 252:1705–1708.

Watson, et al., "A Homing Receptor–IgG Chimera as a Probe for Adhesive Ligands of Lymph Node High Endothelial Venules," *J. Cell. Biol.*, (1990) 110:2221–2229.

Fiete et al., "A Hepatic Reticuloendothelial Cell Receptor Specific for $SO_4$–4GalnAcβ1, 4GlcNAcβ1, 2Manα That Mediates Rapid Clearance of Lutropin," *Cell*, (1991) 67:1103–1110.

Roche, et al., "Molecular Basis of Symbiotic Host Specificity in Rhizobium meliloti: nodH and nodPQ Genes Encode the Sulfation of Lipo–Oligosaccharide Signals," *Cell*, (1991) 67:1131–1143.

Kjellén, et al., "Proteoglycans: Structures and Interactions," *Ann. Rev. Biochem.*, (1991) 60:443–475.

Lowe, et al., "ELAM–1–Dependent Cell Adhesion to Vascular Endothelium Determined by a Transfected Human Fucosylatransferase cDNA," *Cell*, (1990) 63:475–484.

Phillips, et al., "ELAM–1 Mediates Cell Adhesion by Recognition of a Carbohydrate Ligand, Sialyl–Le$^x$", *Science*, (1990) 250:1130–1132.

Walz, et al., "Recognition by ELAM–1 of the Sialyl–Le$^x$ Determinant on Myeloid and Tumor Cells," *Science*, (1990) 250:1132–1135.

Tiemeyer, et al., "Carbohydrate ligands for endothelial–leukocyte adhesion molecule 1," *Proc. Natl. Acad. Sci. USA*, (1991) 88:1138–1142.

Polley, et al., "CD62 and Endothelial Cell–leukocyte Adhesion Molecule 1 (ELAM–1) Recognize the Same Carbohydrate Ligand, Sialyl–Lewis x," *Proc. Natl. Acad. Sci. USA* (1991) 88:6224–6228.

Foxall, et al., "The Three Members of the Selectin Receptor Family Recognize a Common Carbohydrate Epitope, the Sialyl Lewis$^x$" Oligosaccharide, *J. Cell. Biol.*, (1992) 117(4):895–902.

SULFATE LIGANDS FOR L-SELECTINS AND METHODS OF PREVENTING SULFATE ADDITION

GOVERNMENT RIGHTS

The United States Government may have certain rights in this application pursuant to Grant No. GM-23547 awarded by the National Institute of Health.

CROSS-REFERENCE TO RELATED APPLICATIONS

This application is a continuation of U.S. application Ser. No. 07/943,817, filed Sep. 11, 1992, now abandoned, which application is incorporated herein by reference in its entirety and to which application we claim priority under 35 U.S.C. §120.

FIELD OF THE INVENTION

The present invention relates generally to sulfated ligands and to methods of preventing the metabolic addition of a sulfate to a natural ligand or remove a sulfate to thereby prevent the attachment of the ligand to a receptor. More specifically, the invention relates to sulfated forms of sialyl-Lewis X and related oligosaccharides and to locally administering compounds such as non-toxic chlorates which metabolically prevent the addition of a sulfate moiety to an L-selectin ligand resulting in desirable effects such as alleviation of inflammation.

BACKGROUND OF THE INVENTION

There have been a number of research efforts investigating the role of carbohydrates in physiologically relevant recognition. (See Brandley, B. K., and Schnaar, R. L., *J. Leuk. Biol.* (1986) 40:97; and Sharon, N., and Lis, H., *Science* (1989) 246:227). Oligosaccharides are well positioned to act as recognition molecules due to their cell surface location and structural diversity. Many oligosaccharide structures can be created through the differential activities of a smaller number of glycosyltransferases. Their diverse structures, then, can be generated with relatively few gene products, suggesting a plausible mechanism for establishing the information necessary to direct a wide range of cell-cell interactions. Examples of differential expression of cell surface carbohydrates and putative carbohydrate binding proteins (lectins) on interacting cells have been described (see Dodd, J., and Jessel, T. M., *J. Neurosci.* (1985) 5:3278; Regan, L. J., et al., *Proc. Natl. Acad. Sci. USA* (1986) 83:2248; Constantine-Paton, M., et al., *Nature* (1986) 324:459; and Tiemeyer, M., et al., *J. Biol. Chem.* (1989) 263:1671). Further, the question has been raised as to the nature of the leukocyte receptor for ELAM-1 (see Bevilacqua et al. *Proc. Natl. Acad. Sci. USA* (1987) 84:9238).

Tumor associated glycolipids have been reported in fetal tissue and a variety of human cancers, including CML cells (Fukuda, M. N., et al., *J. Biol. Chem.* (1986) 261:2376; Magnani, J. L., et al., *J. Biol. Chem.* (1982) 257:14365; Hakomori, S., et al., *Biochem. Biophys. Res. Comm.* (1983) 113:791). This has led to the hypothesis that these structures may be important in many developmental and oncogenic processes (J. L. Magnani et al., J. Biol. Chem. (1982) 257:14365). Smaller quantities of most of these carbohydrates can be found in normal human tissue (see Fukushi, Y., et al., *J. Exp. Med.* (1984) 160:506), but until now no function for these structures has been reported.

Adhesion of circulating leukocytes to stimulated vascular endothelium is a primary event of the inflammatory response. Several receptors have been implicated in this interaction, including a family of putative lectins that includes gp90$^{MEL}$ (Leu8), GMP-140 (PADGEM) and ELAM-1 (Gong, J.-G., et al., *Nature* (1990) 343:757; Johnston, G. I., et al., *Cell* (1989) 56:1033; Geoffroy, J. S., and Rosen, S. D., *J. Cell Biol.* (1989) 109:2463; Lasky, L. A., et al., *Cell* (1989) 56:1045). While these receptors each contain a domain with sequence homology to calcium dependent lectins, only gp90$^{MEL}$ has been demonstrated to recognize a carbohydrate (see J. S. Geoffroy et al., *J. Cell Biol.* (1989) 109:2463). Endogenous ligands for these receptors have yet to be identified.

ELAM-1 is interesting because of its transient expression on endothelial cells in response to IL-1 or TNF (Bevilacqua, M. P., et al., *Science* (1989) 243:1160). The time course of this induced expression (2–8 h) suggests a role for this receptor in initial neutrophil extravasation in response to infection and injury. Furthermore, Bevilacqua et al. (see Bevilacqua, M. P., et al., *Proc. Natl. Acad. Sci. USA* (1987) 84:9238) have demonstrated that human neutrophils or HL-60 cells will adhere to COS cells transfected with a plasmid containing a cDNA encoding for the ELAM-1 receptor.

Recently, several different groups have published papers regarding ELAM-1 ligands which ligands are also referred to as LECAM-2 ligands. Lowe et al. (1990) demonstrated a positive correlation between the LECAM-2 dependent adhesion of HL-60 cell variants and transfected cell lines, with their expression of the sialyl Lewis x (sLex) oligosaccharide, Neu NAc α2–3Gal-β1–4(Fuc α1–3)-GlcNAc. By transfecting cells with plasmids containing an α(1,3/1,4) fucosyltransferase, they were able to convert non-myeloid COS or CHO lines into sLex-positive cells that bind in an LECAM-2 dependent manner. Attempts to block LECAM-2 dependent adhesion using anti-sLex antibodies were uninterpretable due to the agglutination of the test cells by the antibody. They conclude that one or more members of a family of oligosaccharides consisting of sialylated, fucosylated, lactosaminoglycans are the ligands for the lectin domain of LECAM-2. Phillips et al. (1990) used antibodies with reported specificity for sLex to inhibit the LECAM-2 dependent adhesion of HL-60 or LEC11 CHO cells to activated endothelial cells. Liposomes containing difucosylated glycolipids with terminal sLex structures inhibited adhesion, while those containing nonsialylated Lex structures were partially inhibitory. Walz et al. (1990) were able to inhibit the binding of a LECAM-2-1gG chimera to HL-60 cells with a monoclonal antibody directed against sLex or by glycoproteins with the sLex structure, but could not demonstrate inhibition with CD65 or CD15 antibodies. Both groups concluded that the sLex structure is the ligand for LECAM-2.

Information regarding the DNA sequences encoding endothelial cell-leukocyte adhesion molecules are disclosed in PCT published application WO90/13300 published Nov. 15, 1990. The PCT publication cites numerous articles which may be related to endothelial cell-leukocyte adhesion molecules. The PCT publication claims methods of identifying ELAM-ligands, as well as methods of inhibiting adhesion between leukocytes and endothelial cells using such ligands and specifically refers to MILAs which are described as molecules involved in leukocyte adhesion to endothelial cells.

LECAM-1 is interesting because of its involvement in lymphocytic and neutrophil influx (Watson et al., *Nature* (1991) 349:164–167). It was expressed in chronic lymphocytic leukemia cells which bind to HEV (see Spertini et al., *Nature* (1991) 349:691–694). It is believed that HEV-like structures at sites of chronic inflammation are associated with the symptoms of disease such as rheumatoid arthritis, psoriasis, and multiple sclerosis.

A broad range of ELAM-1 ligands are disclosed in PCT/US91/05416 published as WO 92/02527 (published 20 Feb. 1992) to Brandley et al. and in PCT/US90/02357 published as WO 90/13300 (published 15 Nov. 1990) to Hession et al. both of which are incorporated herein by reference in their entirety and specifically to disclose oligosaccharide structures which reportedly act as ELAM-1 and LECAM-1 ligands.

The earlier studies have largely focused on which oligosaccharide compounds can act as ligands. The present inventors have determined that attachment of a sulfate moiety to the oligosaccharide compound has a significant effect on the ability of the compound to act as a ligand and thereby developed the present invention.

SUMMARY OF THE INVENTION

Sulfated oligosaccharides are disclosed which can be formulated with excipient carrier into pharmaceutical compositions. The compositions can be administered to a patient (preferably by injection) to treat a variety of conditions including inflammation associated with trauma and with the symptoms of diseases such as rheumatoid arthritis, psoriasis, and multiple sclerosis. The presence of a sulfate group has been found to play an important role in the attachment of a natural L-selectin ligand to its receptor. The metabolic addition of a sulfate to the ligand can be prevented by the addition of a compound such as a chlorate and a sulfate can be removed by the inclusion of a specific sulfatase enzyme. Accordingly, L-selectin ligand/receptor binding can be significantly reduced by the administration of a compound which effectively inhibits the addition of a sulfate (such as a chlorate) either systemically or locally to thereby alleviate a condition associated with excessive leukocyte cell to endothelial cell binding. A similar effect can be obtained by administering a compound which removes a sulfate from the naturally sulfated ligand.

An object of the invention is to provide sulfated ligands and pharmaceutical compositions comprising such ligands formulated with acceptable excipient carriers.

Another object is to provide a method of alleviating inflammation by administering a compound such as a chlorate which metabolically inhibits the addition of a sulfate moiety to a natural L-selectin ligand.

Still another object is to provide a method of alleviating inflammation by administering a compound such as a sulfatase which is an enzyme which specifically removes the sulfate moiety from a natural L-selectin ligand.

Yet another object of the present invention is to provide pharmaceutical formulations suitable for inhalation comprised of pharmaceutically acceptable excipient carriers combined with an active ingredient in the form of a sulfatase enzyme which is capable of removing the sulfate moiety from a selectin ligand which enzyme may be extracted from any suitable source and purified or recombinantly produced.

Yet another object is to provide a pharmaceutical formulation comprised of any combination of the (1) sulfated ligands, (2) a compound which metabolically inhibits the addition of a sulfate moiety to a natural L-selectin ligand and (3) a sulfatase which removes a sulfate from the ligand with (4) a pharmaceutically acceptable excipient carrier.

An advantage of the invention is that the sulfated ligands can be used to effectively reduce inflammation by blocking natural receptors, acting as agonists and thereby preventing inflammation.

Another advantage is that the inflammatory effects caused by natural ligands can be alleviated by administering a compound which metabolically inhibits the addition of a sulfate moiety to a natural L-selectin ligand and thereby reduces inflammation.

Another advantage of the invention is that inflammatory effects caused by natural sulfated ligands can be reduced by administering an enzyme in the form of a sulfatase which specifically removes the sulfate moiety from a natural L-selectin ligand.

Yet another advantage of the invention is that a combined effect on reducing inflammation can be obtained by administering combinations of two or more of (1) a sulfated ligand agonist, (2) a compound which metabolically inhibits the addition of a sulfate moiety to a natural L-selectin ligand, and (3) an enzyme which specifically removes a sulfate moiety from a natural ligand.

A feature of the invention is that the sulfated ligands can be readily produced by sulfating known oligosaccharides using known procedures.

Another feature of the invention is that the chlorate used to metabolically prevent the addition of sulfates and sulfatase which removes a sulfate can be used without toxic side effects.

Yet another feature is that by administering both the sulfated ligand agonists, chlorates, and sulfatase together, smaller amounts of each can be used while obtaining the desired anti-inflammatory effect with reduced chances of adverse side-effects.

The sulfated ligand agonists can be bound to anti-inflammatory drugs or detectable labels and/or formulated to provide, for example, compositions useful in assaying a sample for the presence of selectin receptors, compositions useful in detecting the site of inflammation in a patient, or pharmaceutical compositions useful in treating acute inflammation (or treating the inflammatory symptoms of certain diseases) or affecting other phenomena involving the interaction of ligands and selectin receptors.

An important aspect of the invention is pharmaceutical compositions which are useful in treating, preventing and/or alleviating any undesirable effects resulting from the interaction of circulating neutrophils and endothelial cells. Such compositions are comprised of an inactive ingredient in the form of a pharmaceutically acceptable excipient material and at least one, but may include a plurality of, sulfated ligands capable of binding to a selectin receptor.

Still another object is to provide a composition comprising a sulfated ligand which is labeled and which can be used to assay for the presence of a selectin receptor in a sample.

These and other objects, advantages and features of the present invention will become apparent to those persons skilled in the art upon reading the details of the structure, formulation and usage as more fully set forth below, references being made to the accompanying figures and general structural formulae forming a part hereof wherein like symbols refer to like molecular moieties throughout.

BRIEF DESCRIPTION OF THE DRAWINGS

This invention may be better understood and its numerous objects, advantages and features will become apparent to those skilled in the art by reference to the accompanying drawings as follows.

MODES OF CARRYING OUT THE INVENTION

Figure 1:
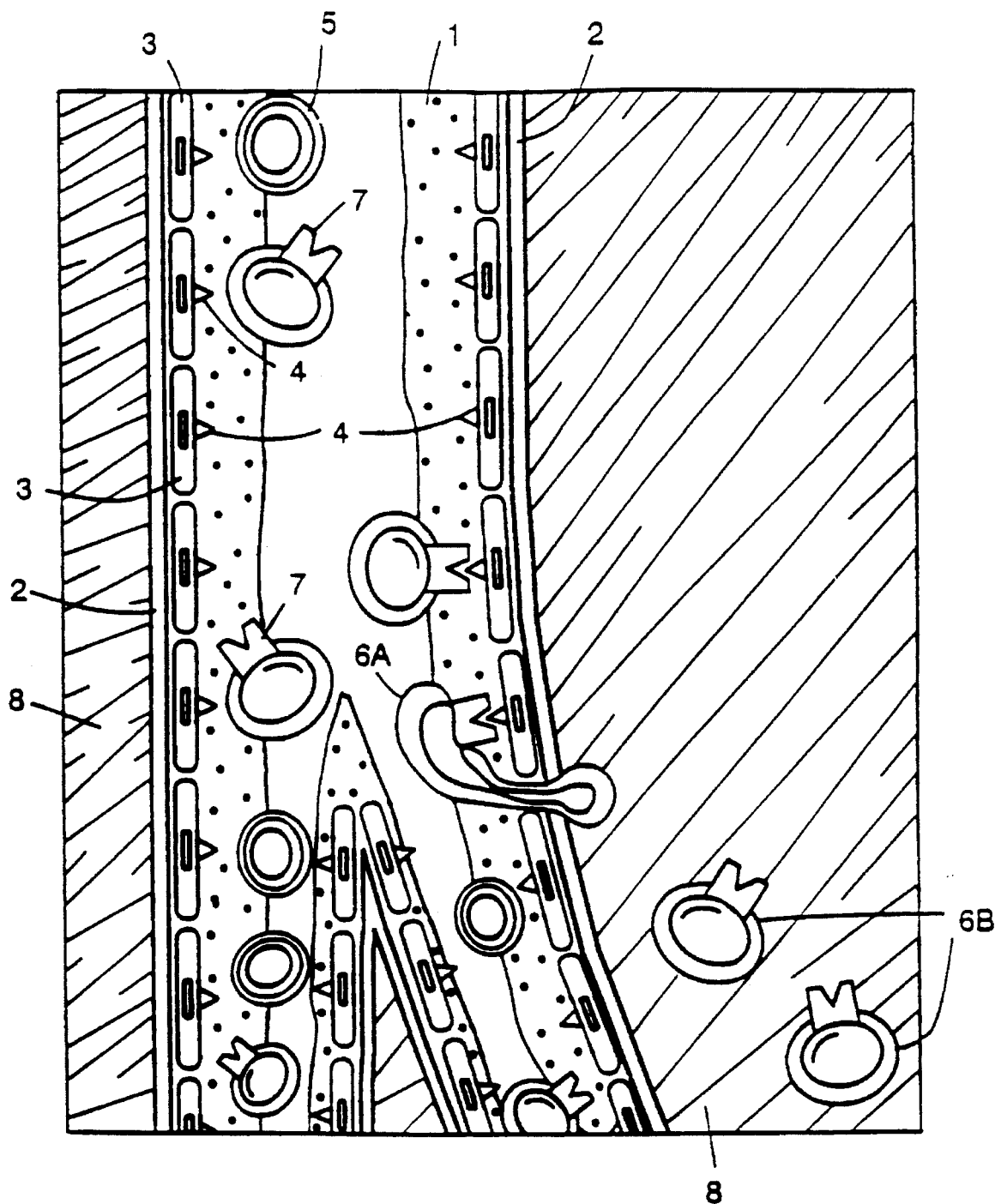
FIG. 1 is a cross-sectional schematic view showing the interaction between white blood cells and activated endothelial cells.

Before the present sulfated ligands and composition containing such ligands and processes for isolating and using such are described, it is to be understood that this invention is not limited to the particular compositions, methods or processes described as such compositions and methods may, of course, vary. It is also to be understood that the terminology used herein is for the purpose of describing particular embodiments only, and is not intended to be limiting since the scope of the present invention will be limited only by the appended claims.

As used in this-specification and the appended claims, the singular forms "a", "an" and "the" include plural referents unless the context clearly dictates otherwise. Thus, for example, reference to "a sulfated ligand" and "a sulfatase" includes mixtures of such ligands and sulfatases, reference to "an ELAM-1" includes reference to mixtures of such molecules, reference to "the formulation" or "the method" includes one or more formulations, methods and/or steps of the type described herein and/or which will become apparent to those persons skilled in the art upon reading this disclosure and so forth.

Some standard abbreviations used in connection with the present invention include: BSA, bovine serum albumin; DEAE, diethylaminoethyl; DMSO, dimethylsulfoxide; ELAM-1, endothelial/leukecyte adhesion molecule-1 (also E-selectin); HPTLC, high performance thin layer chromatography; LECAM-1, leukocyte/endothelial cell adhesion molecule-1 (also L-selectin); MOPS, 3-[N-Morpholino]propanesulfonic acid; NANA, N-acetylneuraminic acid; PVC, polyvinylchloride; TLC, thin layer chromatography; TFA, trifluoroacetic acid; Tris, tris (hydroxymethyl) aminomethane.

A. General Overview

The present inventors have investigated the importance of sulfate groups on ligands which bind to selectins and in particular L-selectins and made certain discoveries which form the basis of the present invention. Firstly, sulfated ligands are disclosed which are sulfated forms of sialyl-Lewis X, sialyl-Lewis A and related oligosaccharides. Preferred ligands of the invention have one of the four following general structural formulae I(a), I(b), I(c) or I(d):

Sialyl Lewis X-Related Structures

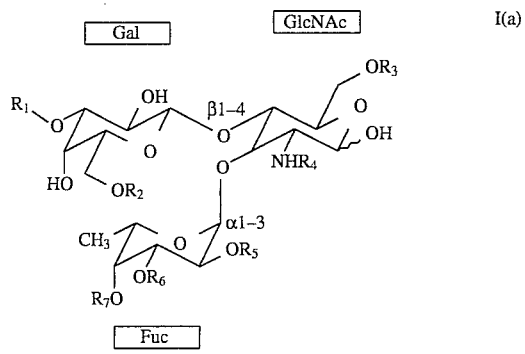

I(a)

wherein $R_1$ is H, $SO_3^-$, or NeuAc; $R_2$ is H, $SO_3^-$, or NeuAc; $R_3$ is H or $SO_3^-$; $R_4$ is Acetyl or $SO_3^-$; $R_5$ is H or $SO_3^-$; $R_6$ is H or $SO_3^-$; $R_7$ is H or $SO_3^-$; with the proviso that at least one of $R_1$–$R_7$ is $SO_3^-$. Here as in the other structures, the abbreviation Ac as shown in the structural formula or Acetyl represents an —$COCH_3$ moiety and Neu represents a neuraminic acid of any type which is preferably a sialic acid in any of its possible forms.

With respect to all the structures disclosed and claimed herein it should be noted that the structures are intended to encompass any and all stereoisomers. This statement applies in particular with respect to the positions shown connected by a waved line in the structures I(a), I(b), I(c) and I(d).

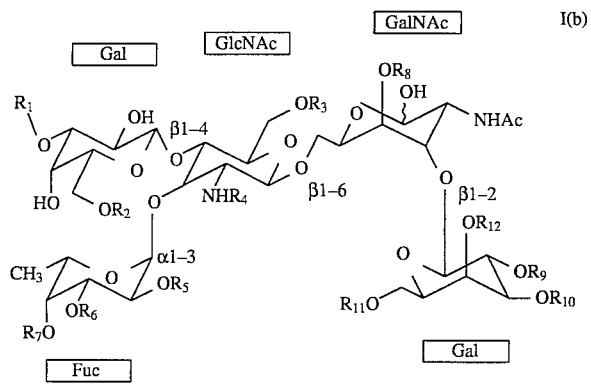

I(b)

wherein $R_1$ is H, $SO_3^-$ or NeuAC; $R_2$ is H, $SO_3^-$ or NeuAC; $R_3$ is H or $SO_3^-$; $R_4$ is Acetyl or $SO_3^-$ ($COCH_3$); $R_5$ is H or $SO_3^-$; $R_6$ is H or $SO_3^-$; $R_7$ is H or $SO_3^-$; $R_8$ is H or $SO_3^-$; $R_9$ is H or $SO_3^-$ or NeuAC; $R_{10}$ is H or $SO_3^-$ or NeuAC; $R_{11}$ is H or $SO_3^-$ or NeuAC; $R_{12}$ is H or $SO_3^-$ or NeuAC; with the proviso that at least one of $R_1$–$R_{12}$ is $SO_3^-$.

Sialyl Lewis A-Related Structures

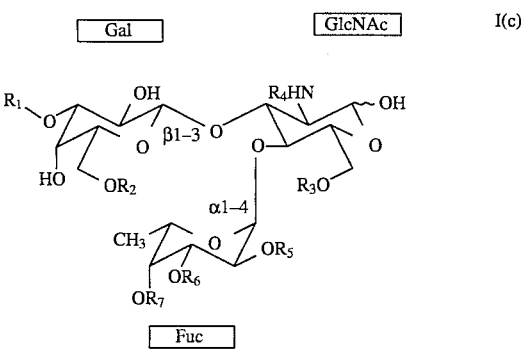

I(c)

wherein $R_1$ is H, $SO_3^-$ or NeuAC; $R_2$ is H, $SO_3^-$ or NeuAC; $R_3$ is H or $SO_3^-$; $R_4$ is Acetyl or $SO_3^-$; $R_5$ is H or $SO_3^-$; $R_6$ is H or $SO_3^-$; $R_7$ is H or $SO_3^-$ with the proviso that at least one of $R_1$—$R_1$ is $SO_3^-$.

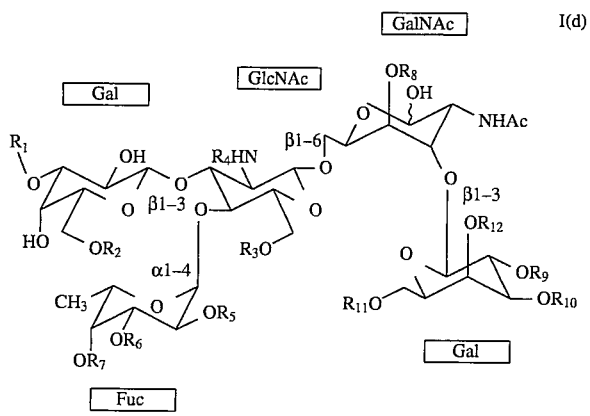

I(d)

wherein $R_1$ is H, $SO_3^-$ or NeuAC; $R_2$ is H, $SO_3^-$ or NeuAC; $R_3$ is H or $SO_3^-$; $R_4$ is Acetyl or $SO_3^-$; $R_5$ is H or $SO_3^-$; $R_6$ is H or $SO_3^-$; $R_7$ is H or $SO_3^-$; $R_8$ is H or $SO_3^-$; $R_9$ is H, $SO_3^-$ or NeuAC; $R_{10}$ is H, $SO_3^-$ or NeuAC; $R_{11}$ is H, $SO_3^-$ or NeuAC; $R_{12}$ is H, $SO_3^-$ or NeuAC with the proviso that at least one of $R_1$-$R_{12}$ is $SO_3^-$.

Secondly, methods of inhibiting the metabolic sulfation of natural L-selectin ligands are taught which methods alleviate inflammation as a result of the unsulfated natural ligand's inability to bind to the natural receptors.

Thirdly, methods of alleviating inflammation are described wherein sulfatase enzymes are administered to the patient in order to remove sulfate moieties on natural L-selectin ligands.

Fourth, pharmaceutical formulations are taught which contain the sulfated ligands, sulfatases which remove sulfates and/or compounds such as chlorates which inhibit the metabolic sulfation of natural ligands. The invention includes a number of additional aspects such as methods of treatment using the sulfated ligands, sulfatases and/or chlorates too alleviate inflammation. In order to understand the general operation of the invention, the following explanation is provided.

FIG. 1 shows a cross-sectional view of a blood vessel 1. The vessel wall 2 is lined internally with endothelial cells 3. The white blood cells 6 can be activated causing the cells 6 to synthesize LECAM-1 which is displayed in FIG. 2 as a surface receptor 7. Both red blood cells 5 and white blood cells 6 flow in the vessel 1. The white blood cells 6 display a receptor 7 which have chemical and physical characteristics which allow the receptor 7 to bind to the ligand 4 on the endothelial cells 3. Once the receptor 7 binds to the ligand 4, the white blood cell 6 is brought through the vessel wall 2 as is shown-with the white blood cell 6A. The white blood cells 6B brought into the surrounding tissue 8 can have positive effects, such as fighting infection, and negative effects, such as inflammation. The present inventors have found that natural ligands 4 includes sulfates and that (1) it is possible to inhibit the sulfation of the natural ligand by introducing a competing moiety such as a chlorate which inhibits sulfation and (2) the sulfate can be removed by the addition of a sulfatase to thereby prevent binding of the natural ligand and receptor.

Figure 2:
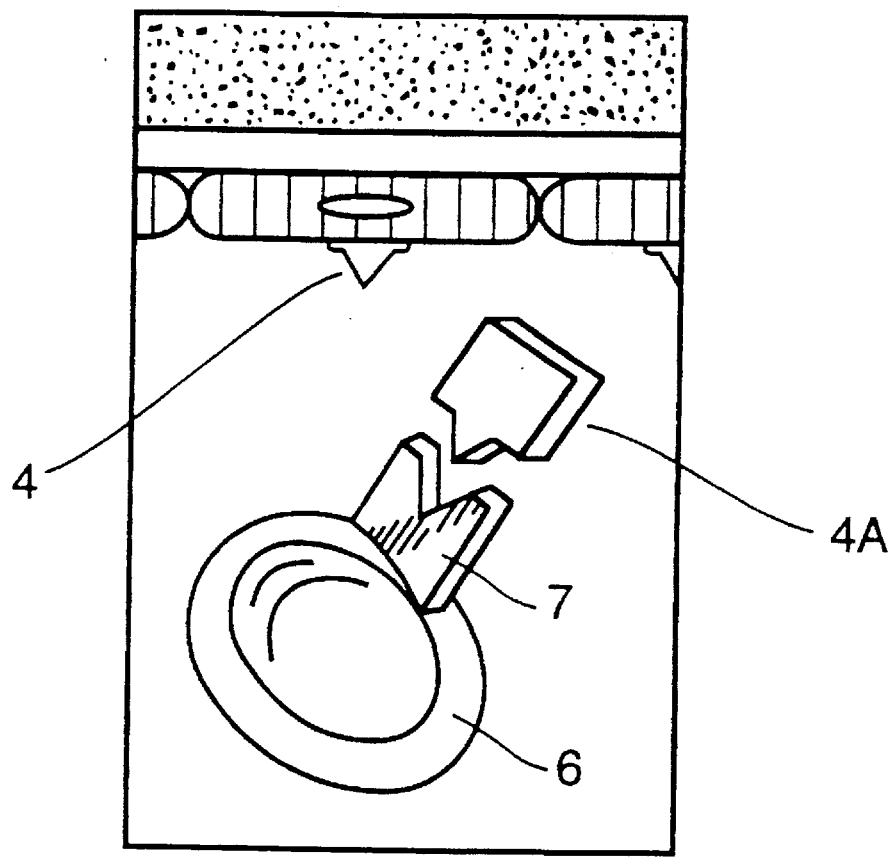
FIG. 2 is a cross-sectional schematic view showing how sulfated ligands of the invention might be used as pharmaceuticals to block LECAM-1.

FIG. 2 shows how the sulfated ligands of the invention, 4A adhere to selectin receptors 7 and can be formulated into pharmaceutical compositions, which when administered will effectively block the selectin receptor, e.g., LECAM-1 and prevent the adhesion of a receptor 7 connected to a white blood cell 6 to a natural ligand 4 on an endothelial cell 3. By administering pharmaceutically effective amounts of sulfated ligands 4A, some, but not all, of the white blood cells will not reach the surrounding tissue 8. By slowing the rate at which the white blood cells reach the surrounding tissue, inflammation can be prevented and/or alleviated.

Although it is not shown within FIGS. 1 and 2, the endothelial cells 3 also generate a receptor when correctly stimulated. This receptor can also attach to a ligand and cause adhesion between the white blood cell and the endothelial cell. Accordingly, by blocking the receptor on the endothelial cell with a synthetic ligand, it is possible to alleviate inflammation in the same manner as suggested above. To a certain extent, ELAM-1 receptors and LECAM-1 receptors will adhere to the same ligand. Accordingly, sulfated ligands of the present invention can be used to block receptors on the white blood cells and simultaneously block receptors on endothelial cells.

It is known that for an acute inflammatory response to occur, circulating neutrophils must bind to and penetrate the vascular wall and access the site of injury. Several molecules have been implicated in this interaction, including a family of putative carbohydrate ligands and their receptors. A group of carbohydrate ligands for endothelial leukocyte adhesion molecule-1 (hereinafter ELAM-1) are disclosed in PCT/US91/05416 published 20 Feb. 1992 as WO 92/02527. The present invention provides a family of sulfated ligands.

An adhesion assay described in WO 92/02527 can be used to obtain a mixture of molecules which adhere to a selectin receptor which molecules can be sulfated. The invention encompasses those sulfated molecules and variations thereof which adhere to ELAM-1 receptors and/or other selectin receptors in this assay.

In accordance with the above description and the schematic diagrams of FIGS. 1 and 2, it can be seen how the sulfated ligands of the present invention can act as agonists in order to prevent and/or alleviate inflammation. Two other aspects of the invention can also be described by reference to FIGS. 1 and 2. More specifically, by including a compound such as a chlorate which prevents sulfation of the ligand, the ligand 4 would not be sulfated and therefore would have a configuration such that it would not adhere to the receptor 7 thereby preventing or alleviating inflammation. Further, after the ligand 4 was formed with sulfates thereon, a sulfatase could be added in order to remove the sulfates and cause the same effect. Since ligands which attach to LECAM-1 receptors also attach to ELAM-1 receptors, the same effect would be expected with respect to all types of selectin receptors. Accordingly, by combining sulfated ligand agonists of the invention with chlorates and sulfatases, a combined effect can be obtained with respect to preventing the adhesion between the white blood cells and the endothelial cells which combined effect can prevent and/or alleviate inflammation.

In order to utilize any of (1) the sulfated ligands, (2) the chlorides, or (3) the sulfatase enzyme the compound may be taken by itself or in combination with the others and formulated into a pharmaceutical formulation by combining any of the above compounds with a pharmaceutically acceptable excipient carrier. With respect to the sulfatase enzymes it should be pointed out that these enzymes can be extracted from natural sources or produced recombinantly. After extraction or recombinant production the sulfatase is purified using methodology known to those skilled in the art such as using high performance liquid chromatography. The sulfatase enzymes may be extracted from sources such as bacteria, invertebrates, mammalian sources such as liver, kidney and leukocytes or endothelial cells. The sulfatase enzyme extracted and/or recombinantly produced is the enzyme which naturally removes sulfate moieties from natural ligands for L-selectins. The functionality of extracted or recombinantly produced enzymes can be readily confirmed by placing the enzyme in contact with sulfated ligands under appropriate conditions and determining the degree of removal of the sulfate moieties from the ligands.

The Effect of Sulfation on Ligands

L-selectin is a receptor present on all leukocytes and known to be involved in leukocyte attachment to endothelia. L-selectin functions as a calcium dependent lectin-like receptor (Lasky et al. Cell 56, 1045, 1989; Imai et al. J. Cell Biol. 111, 1225, 1990). Others (Imai et al. J. Cell Biol. 113, 1213, 1991) have identified two endothelial ligands for L-selectin on lymph note high endothelial venules (HEV) as sulfated, fucosylated, and sialylated glycoproteins called Sgp50 and Sgp90 (sulfated glycoproteins of 50 kD and 90 kD).

Sgp50 has recently been molecularly cloned and shown to be a mucin-like glycoprotein with extensive O-linked carbohydrate chains. Sgp50 has been given the designation GlyCAM. Sialic acid on both Sgp50 and Sgp90 is required for their interaction with L-selectin. Several fortuitous carbohydrate-based inhibitors of L-selectin such as fucoidin and sulfatide are sulfated. Sulfate is required (but not sufficient) for binding activity (Imai et al. J. Cell Biol. 111, 1225, 1990). Examples exist where sulfate modifications of carbohydrate chains are essential for ligand activity (Lerouge et al. Nature 344, 781, 1990; Fiete et al. Cell 67, 1103).

Chlorate is a metabolic inhibitor of carbohydrate sulfation (Baeuerle and Huttner, Biochem Biophys. Res. Comm. 141, 870, 1986). Accordingly, chlorate was used to test whether sulfation is required for the ligand binding activity of GlyCAM. When tests were carried out it was found that the presence of chlorate in organ cultures of lymph nodes substantially reduced (≈90%) sulfation of GlyCAM (and Spg90) and completely eliminated binding to L-selectin. Binding of GlyCAM to a sialic acid specific lectin (Limax agglutinin) or to a fucose-specific lectin (*Aleuria aurantia*) was reduced by exactly the same extent as the sulfation, indicating that sialylation and fucosylation of the molecule were not altered by the presence of chlorate.

By measuring incorporation of $[^3H]$-fucose into GlyCAM directly, it was confirmed that the level of fucosylation was not affected by chlorate. It was also demonstrated that chlorate did not affect the rate of synthesis of the protein core of GlyCAM. Taken together, these results establish that sulfate is required for the interaction of GlyCAM (and Spg90) with L-selectin. In that sialyl-Lewis X (i.e., sLe$^x$) possesses ligand activity for L-selectin it can be deduced that the key carbohydrate chains of GlyCAM involve a sulfate-modification of a sLe$^x$-like oligosaccharide.

L-selectin (LAM-1, LECAM-1, TQ-1, Leu-8, DREG) on leukocytes participates in the initial attachment of lymphocytes, granulocytes, and monocytes to endothelium. Gallatin, W. M., Weissman, I. L. & Butcher, E. C. Nature 303, 30–34 (1983); and Kishimoto, T. K., Jutila, M. A. & Butcher, E. C. Proc. Natl. Acad. Sci. USA 87, 2244–2248 (1990). On lymphocytes, it mediates binding to high endothelial venules (HEV) of lymph nodes during the process of lymphocyte recirculation. L-selectin, as a member of the selectin family of cell-cell adhesion proteins, Stoolman, L. M. Cell 56, 907–910 (1989), functions as a calcium-dependent lectin by recognizing carbohydrate-bearing ligands on endothelial cells. Yednock, T. A., Stoolman, L. M. & Rosen, S. D. J. Cell Biol. 104, 713–723 (1987). Yednock, T. A., Butcher, E. C., Stoolman, L. M. & Rosen, S. D. J. Cell Biol. 104, 725–731 (1987). Bevilacqua, M., et al. Cell 67, 233–233 (1991). Two ligands for L-selectin on lymph node HEV have been identified as sulfated glycoproteins of ≈50K and ≈90K, called Sgp50 and Spg90. Imai, Y., Singer, M. S., Fennie, C., Lasky, L. A. & Rosen, S. D. J. Cell Biol. 111, 2757–2764 (1991). The recently cloned Sgp50, now designated Glycam-1 Lasky, L. A., Singer, M. S., Dowbenko, D., Imai, Y., Henzel, E. J., Fennie, C., Gillett, N., Watson, S. R. & Rosen, S. D. Cell 69, 927–938 (1992), is a novel mucin-like glycoprotein containing predominantly O-linked chains, some of which are sulfated, sialylated and fucosylated.

Previous work has demonstrated that sialylation of Gly-CAM-1 is necessary for ligand activity. Rosen, S. D., Singer, M. S., Yednock, T. A. & Stoolman, L. M. Science 228, 1005–1007 (1985). Imai, Y., Lasky, L. A. & Rosen, S. D. Glycobiology 2, 373–381 (1992). The present inventors have now found that sulfation is also required, indicating that a sulfated oligosaccharide serves as a recognition determinant of GlyCAM-1.

Underlying its function as a calcium-depended lectin, L-selectin possesses a calcium-type (C-type) lectin domain at its extracellular amino terminus preceding an EGF domain, two complement-regulatory-like domains, a transmembrane segment and a short cytoplasmic tail. Lasky, L. A., Singer, M. S., Yednock, T. A., Dowbenko, D., Fennie, C., Rodriguez, H., Nguyen, T., Stachel, S. & Rosen, S. D. Cell 56, 1045–1055 (1989). Siegelman, M. H., Van de Rijn, M. & Weissman, I. L. Science 243, 1165–1172 (1989). Tedder, T. F., Isaacs, C. M., Ernst, T. J., Demetri, G. D., Adler, D. A. & Disteche, C. M. J. Exp. Med. 170, 123–133 (1989). Camerini, D., James, S. P., Stamenkovic, I. & Seed, B. Nature 342, 78–82 (1989). Early work revealed that several sulfated glycoconjugates, such as fucoidin, sea urchin egg jelly fucan and sulfatide could bind L-selectin. Stoolman, L. M. & Rosen, S. D. J. Cell Biol. 96, 722–729 (1983). Imai, Y., True, D. D., Singer, M. S. & Rosen, S. D. J. Cell Biol. 111, 1225–1232 (1990). These findings dictated the choice of $^{35}$S-sulfate as a metabolic precursor to label endothelial ligands for L-selectin and led to the identification of Gly-CAM-1 and Sgp90. These two glycoproteins and perhaps others Berg, E. L., Robinson, M. K., Warnock, R. A. & Butcher, E. C. J. Cell Biol. 114, 343–349 (1991) are targets of the adhesion-blocking mAb called MECA-79. Streeter, P. R., Rouse, B. T. N. & Butcher, E. C. J. Cell Biol. 107, 1853–1862 (1988). GlyCAM-1 is found in detergent lysates of lymph nodes and as a soluble form in conditioned medium of cultured lymph node slices. The mucin character of GlyCAM-1 suggests a functional organization in which the polypeptide backbone serves to present O-linked chains in a highly clustered form to the lectin domain of L-selectin. Some of the O-linked chains of GlyCAM-1 are sialylated, fucosylated, and sulfated. Sialic acid is clearly required for ligand activity, since treatment of GlyCAM-1 with broad spectrum and linkage-specific sialidases largely eliminates its binding to L-selectin. An essential role for fucose has also been inferred based on competition binding assays with defined oligosaccharides.

In developing the present inventions, the inventors investigated whether sulfation of the carbohydrate chains is required for the ligand activity of GlyCAM-1. Early experiments failed to identify a commercially available arylsulfatase that would remove sulfate from GlyCAM-1. Thereafter, the present inventors carried out metabolic experiments using a chlorate to inhibit ATP-sulfurylase, the first enzyme in the synthesis of the high energy donor of sulfate (PAPS). Baeuerle, P. A. & Huttner, W. B. Biochem. Biophys. Res. Commun. 141, 870–877 (1986). Chlorate acts as an effective inhibitor of the sulfation of both N-linked and O-linked carbohydrate chains, while not affecting protein synthesis or having cytopathic effects. Rapraeger, A., C., Krufka, A. & Olwin, B. B. Science 252, 1705–1708 (1991).

Inhibiting the Metabolic Sulfation of L-selectins

Slices of mouse lymph nodes were cultured with $^{35}$S-sulfate in the presence and absence of 10 mM chlorate. Detergent lysates were prepared and subjected to precipitation with several reagents that recognize GlyCAM-1. With a peptide antibody that binds to the polypeptide core of GlyCAM-1, the amount of labeled GlyCAM immunoprecipitated from the chlorate-treated culture was substantially reduced compared to that of the control culture. As determined by direct scintillation counting, chlorate treatment reduced the radioactivity immunoprecipitated by the peptide antibody to 12% of the control level. Culture in chlorate resulted in a similar reduction in the amount of $^{35}$S-sulfate precipitated by Limax agglutinin (11.4% of control) and *Aleuria aurentia* lectin (13.7% of control), lectins that react with sialic acid and fucose, respectively. SDS-PAGE analysis demonstrated that this reduction was reflected in the commensurately reduced autoradiographic intensity of GlyCAM-1, although there were additional components in the precipitates. In contrast to these findings, LEC-IgG, the immunoglobulin chimera of L-selectin Watson, S. R., Imai, Y., Fennie, C., Geoffroy, J. S., Rosen, S. D. & Lasky, L. A. *J. Cell Biol.* 110, 2221–2229 (1990) failed to precipitate a detectable GlyCam-1 band from the chlorate-treated culture, whereas a strong band was seen in the control. Only a background level (0.9% of control) of radioactivity was measured in the precipitate from the chlorate-treated culture.

The simplest interpretation of these findings was that chlorate, as a consequence of its general inhibition of sulfation, reduced sulfate incorporation into GlyCAM-1 to about 10–15% of the control, as inferred from the ratio of counts precipitated by the peptide antibody. There was no apparent effect of chlorate on the overall sialylation or fucosylation of the molecule, since the reduction in Aleuria and Limax precipitated $^{35}$S—SO$_4$ counts closely paralleled the reduction in sulfate incorporation. However, the binding of LEC-IgG to GlyCAM, which represents the functional interaction of interest, was completely abrogated by culture in chlorate.

Other Effects of Chlorate on L-selectin

To determine directly whether the fucosylation of GlyCAM-1 was affected by chlorate, $^3$H-fucose was employed as a metabolic precursor. The peptide antibody precipitated approximately the same number of cpm from detergent lysates obtained from the chlorate and control cultures; moreover, the autoradiographic intensity of the GlyCAM-1 component was comparable in both conditions. However, while LEC-IgG precipitated GlyCAM-1 in the control culture, LEC-IgG precipitated only a background level of counts (7% of control) from the chlorate-treated culture and there was no detectable GlyCAM-1.

To determine what effect chlorate had on the synthesis of the protein core of GlyCAM-1, the present inventors employed $^3$H-threonine as a metabolic label. When conditioned medium was analyzed, LEC-IgG precipitated a prominent GlyCAM-1 component from the control culture but did not react with any components when chlorate was present during the culture. With or without chlorate treatment, two antibodies against the coreprotein of GlyCAM-1 precipitated broad bands that ran at ≈50K. With chlorate the distribution of the bands extended somewhat higher in the gel, possibly reflecting the effect of undersulfation on electrophoretic mobility. When lysates were immunoprecipitated with peptide antibodies, GlyCAM-1 was seen together with several lower molecular weight components. The same pattern was seen with the three independent antibodies. Importantly, culture in chlorate did not significantly alter either the intensity or pattern of the bands except for upward broadening of the highest molecular weight component. It is suspected that the lower molecular weight lysate components represent metabolic precursors to GlyCAM-1. If this speculation is correct, the absence of these components in conditioned medium would suggest that only the mature form of GlyCAM-1 is secreted.

Taken together, these results indicate that chlorate substantially inhibits the sulfation of GlyCAM-1 but allows biosynthesis of the protein core as well as sialylation and fucosylation of its carbohydrate chains to proceed normally. The complete loss of reactivity with LEC-IgG establishes the importance of sulfation for binding. As the O-linked carbohydrate chains of GlyCAM-1 have been shown to be sulfated and the polypeptide has only one potential tyrosine residue for sulfate addition, the present inventors have now concluded that the critical sulfates must be on the carbohydrate chains.

A variety of biological recognition phenomena depend on sulfate modifications of oligosaccharide chains. These include uptake of sulfated pituitary hormones by a hepatic reticuloendothelial receptor, Fiete, D., Srivastava, V., Hindsgaul, O. & Baenziger, J. U. *Cell* 67, 1103–1110 (1991) induction of root nodulation in certain legumes by a bacterially-derived sulfated oligosaccharide Roche, P., Debelle, F., Maillet, F., Lerouge, P., Faucher, C., Truchet, G., Denarie, J. & Prome, J. C. *Cell* 67, 1131–1143 (1991) (see below), the interaction of heparin fragments with anti-thrombin, Kjellen, L. & Lindahl, U. *Ann. Rev. Biochem.* 60, 443–475 (1991) and the binding of basic FGF to cell surface heparan sulfate. The above-described results now extend this array of processes to a cell-cell recognition event by showing a sulfation requirement for GlyCAM-1, a biological ligand for L-selectin.

Previous work has demonstrated that E-selectin, Lowe, J. B., Stoolman, L. M., Nair, R. P., Larsen, R. D., Berhend, T. L. & Marks, R. M. *Cell* 63, 475–484 (1990). Phillips, M. L., Nudelman, E., Gaeta, F., Perez, M., Singhal, A. K., Hakomori, S. & Paulson, J. C. *Science* 250, 1130–1132 (1990). Walz, G., Aruffo, A., Kolanus, W., Bevilacqua, M. & Seed, B. *Science* 250, 1132–1135 (1990). Tiemeyer, M., Swiedler, S. J., Ishihara, M., Moreland, M., Schweingruber, H., Hirtzer, P. & Brandley, B. K. *Proc. Natl. Acad. Sci. (USA)* 88, 1138–1142 (1991) P-selectin, Polley, M. J., Phillips, M. L., Wayner, E., Nudelman, E., Singhal, A. K., Hakomori, S. & Paulson, J. C. *Proc. Natl. Acad. Sci. (USA)* 88, 6224–6228 (1991) and L-selectin Imai, Y., Lasky, L. A. and Rose, S. D. Glycobiology 2, 373–381, 1992; Foxall et al. *J. Cell Biol.* 117, 895–902, 1992 can all recognize the fucosylated and sialylated tetrasaccharide called sialyl Lewis X as well as related carbohydrates. The present inventors now disclose that the generation of a preferred biological ligand for each selectin involves distinctive modifications of a common carbohydrate structure, e.g., the sialyl Lewis X and/or sialyl Lewis A structure and specifically indicate that sulfation is an essential modification for GlyCAM-1. An appropriate analogy may be provided by rhizobia-legume symbiosis, in which modified forms of a lipo-oligosaccharide function as nodulation-inducing signals, with host range defined by the nature of the modification. In the case of *Rhizobia melitoti*, sulfation of the core lipo-oligosaccharide determines the host specificity, whereas in other species different modifications are involved.

Use and Administration

The compounds of the invention such as (1) various chlorates, (2) sulfatases, and (3) sulfated ligands can be administered to a subject in need thereof to treat a patient, i.e., prophylactically preventing inflammation or relieving it after it has begun. The sulfatases as well as chlorates such as sodium or potassium chlorate and/or sulfated ligands are preferably administered with a pharmaceutically acceptable carrier, the nature of the carrier differing with the mode of administration, for example, oral administration, usually using a solid carrier and I.V. administration a liquid salt solution carrier. The formulation and/or means of administration will also vary depending on whether a chlorate, sulfatase or a sulfated ligand is being administered, e.g., a sulfatase is an enzyme which would not generally be administered orally but would be administered by I.V.

The desired formulation can be made using a variety of excipients including, for example, pharmaceutical grades of mannitol, lactose, starch, magnesium stearate, sodium saccharin cellulose, magnesium carbonate, and the like. Oral compositions may be taken in the form of solutions, suspensions, tablets, pills, capsules, sustained release formulations, or powders. Particularly useful is the administration of the sulfated ligand molecules and chlorates directly in transdermal formulations with permeation enhancers such as DMSO. Other topical formulations can be administered to treat dermal inflammation.

A therapeutically effective amount is an amount of sulfated ligand molecules which will bind to a substantial proportional number of the L-selectin receptor so that inflammation can either be prevented or ameliorated. Alternatively, a therapeutically effective amount of a chlorate will prevent sulfation of natural ligands in large enough numbers so as to prevent or alleviate inflammation. Thus, "treating" as used herein shall mean preventing or ameliorating inflammation and/or symptoms associated with inflammation. Typically, the compositions of the instant invention will contain from less than 1% to about 95% of the active ingredient, preferably about 10% to about 50%. Preferably, between about 10 mg and 50 mg will be administered to a child and between about 50 mg and 1000 mg will be administered to an adult. The frequency of administration will be determined by the care given based on patient responsiveness. Other effective dosages can be readily determined by one of ordinary skill in the art through routine trials establishing dose response curves.

In determining the dose of sulfatases, chlorates and/or sulfated ligand agonists to be administered, it must be kept in mind that one may not wish to completely block all of the selectin receptors. In order for a normal healing process to proceed, at least some of the white blood cells or neutrophils must be brought into the tissue in the areas where the wound, infection or disease state is occurring. The amount of the sulfatases, chlorates and/or sulfated ligands administered as blocking agents must be adjusted carefully based on the particular needs of the patient while taking into consideration a variety of factors such as the type of disease that is being treated.

It is believed that the sulfatases, chlorates and/or sulfate ligands of the present invention can be used to treat a wide range of diseases, including diseases such as rheumatoid arthritis, asthma, adult respiratory distress syndrome, sarcoidosis, hypersensitivity pneumonitis and multiple sclerosis. The compositions of the invention should be applicable to treat any disease state wherein the immune system turns against the body causing the white cells to accumulate in the tissues to the extent that they cause tissue damage, swelling, inflammation and/or pain. The inflammation of rheumatoid arthritis, for example, is created when large numbers of white blood cells quickly enter the joints in the area of disease and attack the surrounding tissues.

Formulations of sulfatases, chlorates and/or sulfated ligands might also be administered to prevent the undesirable aftereffects of tissue damage resulting from heart attacks. When a heart attack occurs and the patient has been revived, such as by the application of anticoagulants or thrombolytic (e.g., tPA), the endothelial lining where a clot was formed has often suffered damage. When the antithrombotic has removed the clot, the damaged tissue beneath the clot and other damaged tissue in the endothelial lining which has been deprived of oxygen become activated. The activated white blood cells possess the LECAM-1 receptors. The receptors adhere to ligand molecules on the surface of endothelial cells. The ligand molecules may be induced to the surface of the endothelial cells by activation. Large numbers of white blood cells are quickly captured and brought into the tissue surrounding the affected area, resulting in inflammation, swelling and necrosis which thereby decreases the likelihood of survival of the patient.

In addition to treating patients suffering from the trauma resulting from heart attack, patients suffering from actual physical trauma could be treated with formulations of the invention in order to relieve the amount of inflammation and swelling which normally result after an area of the body is subjected to severe trauma. This is most preferably done by local injection of sulfatases, chlorates and/or sulfated ligand agonists to the area subjected to trauma. Other disease states which might be treatable using formulations of the invention include various types of arthritis and adult respiratory distress syndrome. After reading the present disclosure, those skilled in the art will recognize other disease states and/or symptoms which might be treated and/or mitigated by the administration of formulations of the present invention.

Other modes of administration will also find use with the subject invention. For instance, sulfatases, chlorates, and/or sulfated ligand agonist of the invention can be formulated in suppositories and, in some cases, aerosol and intranasal compositions. For suppositories, the vehicle composition will include traditional binders and carriers such as, polyalkylene glycols, or triglycerides. Such suppositories may be formed from mixtures containing the active ingredient in the range of about 0.5% to about 10% (w/w), preferably about 1% to about 2%.

Intranasal formulations will usually include vehicles that neither cause irritation to the nasal mucosa nor significantly disturb ciliary function. Diluents such as water, aqueous saline or other known substances can be employed with the subject invention. The nasal formulations may also contain preservatives such as, but not limited to, chlorobutanol and benzalkonium chloride. A surfactant may be present to enhance absorption of the subject proteins by the nasal mucosa.

A variety of different respiratory diseases exhibit symptoms which are aggravated by inflammation and all aspects of the present invention can be used in the treatment of such diseases in order to alleviate and/or prevent the aggravation of such symptoms. This is preferably done by the topical pulmonary administration of the sulfated ligand agonists, sulfatases and/or chlorates of the invention. Such compounds can be topically delivered to the passages of the lung surface. Aerosol formulations may be delivered by the use of conventional metered dose inhalers (MDIs). By formulating any or all of the sulfated ligand agonists, sulfatases or chlorates in combination with a suitable propellant and delivering the formulation via an MDI, relief from pulmonary inflammation can be obtained in a very short period of time.

Sulfated ligand agonists, sulfatases and/or chlorate of the invention are preferably administered as injectables. Typically, injectable compositions are prepared as liquid solutions or suspensions; solid forms suitable for solution in, or suspension in, liquid vehicles prior to injection may also be prepared. The preparation may also be emulsified or the active ingredient encapsulated in liposome vehicles.

Suitable excipient vehicles are, for example, water, saline, dextrose, glycerol, ethanol, or the like, and combinations thereof. In addition, if desired, the vehicle may contain minor amounts of auxiliary substances such as wetting or emulsifying agents or pH buffering agents. Actual methods of preparing such dosage forms are known, or will be apparent, to those skilled in the art. See, e.g., Remington's Pharmaceutical Sciences, Mack Publishing Company, Easton, Pa., 17th edition, 1985. The composition or formulation to be administered will, in any event, contain a quantity of the chlorate and/or sulfated agonist adequate to achieve the desired state in the subject being treated.

The various sulfatases, chlorates and sulfated ligand agonists of the present invention can be used by themselves, with each other, or in combination with pharmaceutically acceptable excipient materials as described above. Further, the ligand compounds of the invention can be made as conjugates wherein the sulfated ligands are linked in some manner to a label, e.g., fluorescent, radioactive and enzyme labels. By forming such conjugates, the ligand compounds of the invention act as biochemical delivery systems for the label so that a site of inflammation can be detected.

Sulfated ligand agonists of the invention could also be used as laboratory probes to test for the presence of a selectin in a sample. Such probes are preferably labeled.

EXAMPLES

The following examples are put forth so as to provide those of ordinary skill in the art with a complete disclosure and description of methodologies carried out in order to demonstrate the importance of sulfate groups present on L-selectin ligands with respect to their interaction and/or binding with L-selection receptors. These examples are not intended to limit the scope of what the inventors regard as their invention. Efforts have been made to ensure accuracy with respect to numbers used (e.g., amounts, temperature, etc.) but some experimental errors and deviation should be accounted for. Unless indicated otherwise, parts are parts by weight, molecular weight is weight average molecular weight, temperature is in degrees Centigrade, and pressure is at or near atmospheric.

Unless defined otherwise, all technical and scientific terms used herein have the same meaning as commonly understood by one of ordinary skill in the art to which this invention belongs. Although methods and materials similar or equivalent to those described herein can be used in the practice or testing of the present invention, preferred methods and materials are now described. All publications mentioned herein are incorporated herein by reference.

Example 1

Inhibition of GlyCAM-1 sulfation eliminates its interaction and/or binding with L-selectin. This conclusion was reached when lymph nodes were metabolically labelled in organ culture with (a) [$^{35}$-S]-sulfate or (b) [$^3$-H]-fucose in the presence or absence of chlorate and detergent lysates were subjected to precipitation with L-selectin chimera (LEC-IgG), a rabbit anti-Sgp50 peptide antibody (anti-peptide 2), rabbit preimmune serum, *Limax flavus* agglutinin (sialic acid specificity), or *Aleuria aurantia* agglutinin (AAA; fucose specific). The apparent molecular weight of [$^3$-H]-fucose-labelled GlyCAM-1 was slightly larger in the presence of chlorate, probably because the reduced sulfation retards electrophoretic mobility.

Pooled mesenteric and peripheral lymph nodes from ICR mice (80 mg wet weight per condition) were incubated with (a) 250 uCi of [$^{35}$-S]-sodium sulfate (ICN) or (b) 250 uCi of [5,6 $^3$-H]-L-fucose (ICN) in the presence or absence of 10 mM Na chlorate (Aldrich) in 0.5 ml of RPMI-1640 with 25 mM HEPES (1/10 sulfate concentration) for 4 h at 37° C. Tissue was extracted with 1.2 ml of 2% Triton X-100 (Boehringer Mannheim) in Dulbecco's PBS containing 1 mM PMSF (Sigma), 1% (v/v) aprotinin (Sigman), 10 ug/ml of pepstatin (Boehringer Mannheim) and 0.02% NaN$_3$ (lysis buffer) as described previously[11]. The lysates were boiled 3 min and the supernatants were precleared with 100 ul of Protein A Sepharose (Zymed) overnight. Aliquots of the precleared supernatants were added to 10 ul beads of LEC-IgG-Protein A Sepharose Beads (30 ug LEC-IgG per 10 ul beads), rabbit anti-peptide 2-Protein A beads (10 ul serum per 10 ul beads), rabbit preimmune serum-Protein A beads (10 ul serum per 10 ul beads), *Limax flavus* agglutinin-Sepharose beads (20 ug protein per 10 ul beads), or *Aleuria aurantia* agglutinin-Sepharose beads (10 ug protein per 10 ul beads), and incubated for 4 h at 4° C. on a rocker. The beads were washed in the lysis buffer (6 times), and the 1/14 aliquots of beads were saved for direct counting by a scintillation counting and the remainder of beads were solubilized in Laemmli sample buffer (without beta mercaptoethanol) and run by on a 10% acrylamide gel (nonreducing condition) with fluorography employing ENHANCE (New England Nuclear). Molecular weight markers (BioRad) were phosphorylase B (97.4K), BSA (66.2K), ovalbumin (45K), carbonic anhydrase (31K), soybean trypsin inhibitor (21.5K). LEC-IgG and antiserum were coated on Protein A-Sepharose beads by rocking overnight at 4° C. Lectin beads were prepared by coupling Limax agglutinin (Calbiochem) and AAA (Boehringer Mannheim) to CNBr-activated Sepharose 4B (Sigman). Miller, R. *Meth. Enzymol.* 138, 527–536 (1987).

Example 2

Inhibition of GlyCAM-1 sulfation eliminates its interaction and/or binding with L-selectin. This conclusion was reached when aliquots of the same precipitates of Example 1, labelled with (a) [$^{35}$-S]-sulfate or (b) [$^3$-H]-fucose in the presence (dark bars) or absence (cross-hatched bars) of chlorate were subjected to scintillation counting. The percents shown in a given panel (a) (not shown) indicate the percent counts obtained in the presence of chlorate as compared to the absence of chlorate. The values for anti-peptide 2, Limax, and AAA were essentially the same, reflecting the overall reduction in sulfation. In an independent experiment, the corresponding values were: 6% (for LEC-IgG), 35.6% (for anti-peptide 2), 35.3% (for Limax).

Example 3

Inhibition of GlyCAM-1 sulfation eliminates its interaction and/or binding with L-selectin. This conclusion was reached when lymph nodes were labeled with L-[3-$^3$H]-threonine in the presence or absence of chlorate. Conditioned medium (a) or detergent extracts (b) were subjected to precipitation with LEC-IgG, rabbit anti-Sgp50 anti-peptide antibodies (anti-peptide 1, 2, 3), or rabbit preimmune serum.

Mouse lymph nodes were labeled with 750 uCi of L-[3-$^3$H] threonine (Amersham) in 0.5 ml of threonine free-1/10 sulfate concentration-RPMI 1640 containing 25 mM HEPES for 4 h at 37° C. in the absence or the presence of 10 mM sodium chlorate. Detergent lysates were boiled, precleared and subjected to precipitation with the indicated reagent as described in Example 1. Conditioned media were precleared and precipitated in parallel. The bead-bound material was analyzed on SDS-PAGE under reducing conditions with fluorography. In the anti-peptide antibody lanes, the ≈50K component was compressed by the immunoglobulin heavy chain.

The various aspects of the present invention have been shown and described herein in what is considered to be the most practical, and preferred embodiments. It is recognized, however, that departures may be made therefrom which are within the scope of the invention, and that obvious modifications will occur to one skilled in the art upon reading this disclosure.

We claim:

1. A method of blocking selectin receptor binding to an endothelial cell comprising treating a cell with one or more compounds selected from the group consisting of: a compound encompassed by one of the following general structural formula:

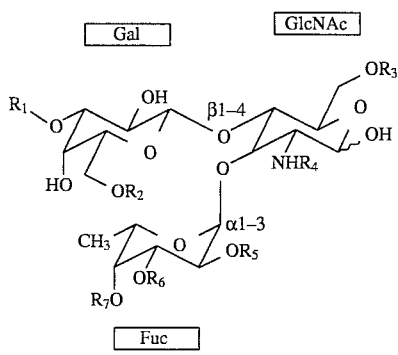

I(a)

wherein $R_1$ is H, $SO_3^-$, or NeuAc; $R_2$ is H, $SO_3^-$, or NeuAc; $R_3$ is H or $SO_3^-$; $R_4$ is Acetyl or $SO_3^-$; $R_5$ is H or $SO_3^-$; $R_6$ is H or $SO_3^-$; $R_7$ is H or $SO_3^-$; with the proviso that at least one of $R_1$–$R_7$ is $SO_3^-$ wherein Ac represents an acetyl moiety and Neu represents a neuraminic acid;

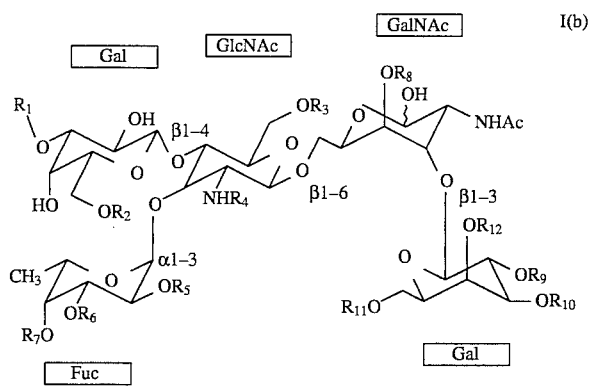

I(b)

wherein $R_1$ is H, $SO_3^-$, or NeuAc; $R_2$ is H, $SO_3^-$, or NeuAc; $R_3$ is H or $SO_3^-$; $R_4$ is Acetyl or $SO_3^-$; $R_5$ is H or $SO_3^-$; $R_6$ is H or $SO_3^-$; $R_7$ is H or $SO_3^-$; $R_8$ is H or $SO_3^-$; $R_9$ is H, $SO_3^-$ or NeuAc; $R_{10}$ is H, $SO_3^-$ or NeuAc; $R_{12}$ is H, $SO_3^-$ or NeuAc; with the proviso that at least one of $R_1$–$R_{12}$ is $SO_3^-$;

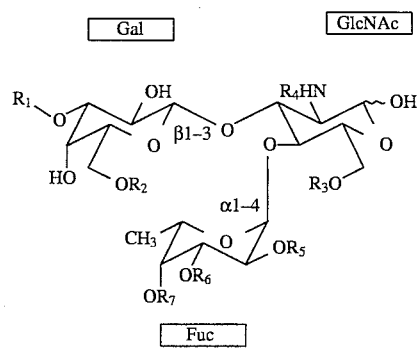

I(c)

wherein $R_1$ is H, $SO_3^-$, or NeuAc; $R_2$ is H, $SO_3^-$, or NeuAc; $R_3$ is H or $SO_3^-$; $R_4$ is Acetyl or $SO_3^-$; $R_5$ is H or $SO_3^-$; $R_6$ is H or $SO_3^-$; $R^7$ is H or $SO_3^-$; with the proviso that at least one of $R_1$–$R_7$ is $SO_3^-$; and

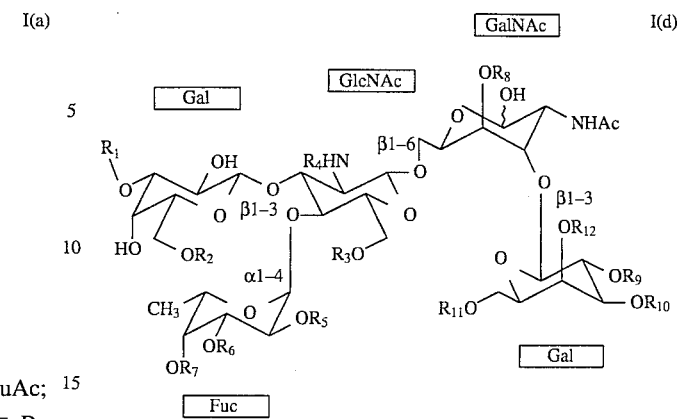

I(d)

wherein $R_1$ is H, $SO_3^-$, or NeuAc; $R_2$ is H, $SO_3^-$, or NeuAc; $R_3$ is H or $SO_3^-$; $R_4$ is Acetyl or $SO_3^-$; $R_5$ is H or $SO_3^-$; $R_6$ is H or $SO_3^-$; $R_7$ is H or $SO_3^-$; $R_8$ is H or $SO_3^-$; $R_9$ is H, $SO_3^-$ or NeuAc; $R_{10}$ is H, $SO_3^-$ or NeuAc; $R_{12}$ is H, $SO_3^-$ or NeuAc; with the proviso that at least one of $R_1$–$R_{12}$ is $SO_3^-$.

2. A method of blocking selectin receptor binding to an endothelial cell comprising treating a cell with one or more compounds selected from the group consisting of: a compound encompassed by one of the following general structural formula:

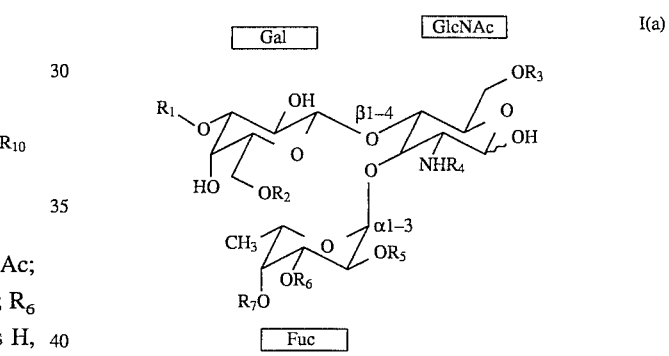

I(a)

wherein $R_1$ is NeuAc; $R_2$ is H or $SO_3^-$; $R_3$ is $SO_3^-$; $R_4$ is Acetyl; $R_5$ is H; $R_6$ is H; $R_7$ is H; wherein Ac represents an acetyl moiety and Neu represents a neuraminic acid; and

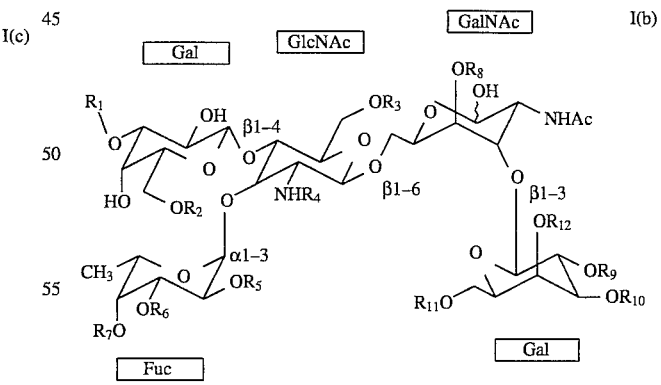

I(b)

wherein $R_1$ is NeuAc; $R_2$ is H or $SO_3^-$; $R_3$ is $SO_3^-$; $R_4$ is Acetyl; $R_5$ is H; $R_6$ is H; $R_7$ is H; $R_8$ is H; $R_9$ is H; $R_{10}$ is NeuAc; $R_{11}$ is H; and $R_{12}$ is H.

* * * * *